US00RE46615E

(19) United States
(12) Reissued Patent
Roholt

(10) Patent Number: US RE46,615 E
(45) Date of Reissued Patent: Nov. 28, 2017

(54) ACCOMMODATING INTRA-OCULAR LENS SYSTEM

(71) Applicant: Vista Ocular, LLC, Canton, OH (US)

(72) Inventor: Philip C. Roholt, Canton, OH (US)

(21) Appl. No.: 14/931,162

(22) Filed: Nov. 3, 2015

Related U.S. Patent Documents

Reissue of:
(64) Patent No.: 8,574,295
Issued: Nov. 5, 2013
Appl. No.: 13/351,459
Filed: Jan. 17, 2012

(51) Int. Cl.
*A61F 2/16* (2006.01)
*A61B 5/0488* (2006.01)
*A61B 5/00* (2006.01)
*A61B 5/0492* (2006.01)

(52) U.S. Cl.
CPC ..... *A61F 2/1635* (2013.01); *A61B 5/04888* (2013.01); *A61B 5/686* (2013.01); *A61F 2/1648* (2013.01); *A61B 5/0492* (2013.01)

(58) Field of Classification Search
USPC ..... 623/6.22, 6.37, 4, 24, 25, 4.1
See application file for complete search history.

(56) References Cited

U.S. PATENT DOCUMENTS 4,373,218 A * 2/1983 Schachar ..... 623/6.13
4,585,457 A 4/1986 Kalb
4,816,031 A 3/1989 Pfoff
5,108,429 A 4/1992 Wiley
5,171,266 A 12/1992 Wiley et al.
5,203,788 A 4/1993 Wiley
5,800,530 A 9/1998 Rizzo, III
6,096,078 A 8/2000 McDonald
6,120,538 A 9/2000 Rizzo, III et al.
6,511,508 B1 * 1/2003 Shahinpoor et al. ..... 623/4.1
6,618,208 B1 9/2003 Silver
6,797,004 B1 9/2004 Brady et al.
7,041,133 B1 5/2006 Azar
7,060,094 B2 6/2006 Shahinpoor et al.
7,118,596 B2 10/2006 Zadno-Azizi et al.
7,198,640 B2 4/2007 Nguyen
(Continued)

OTHER PUBLICATIONS

PCT/US2013/021663 International Search Report and Written Opinion dated Apr. 25, 2013 (12 pages).
(Continued)

*Primary Examiner* — Cary Wehner
(74) *Attorney, Agent, or Firm* — Grasso PLLC

(57) ABSTRACT

An implantable, compressible, accommodating intra-ocular lens (IOL) coupled to at least one sensor which detects a signal created by the ciliary muscle. A ciliary sulcus ring can house the at least one sensor, and the sensor can include miniaturized electrodes (ciliary muscle probes) for implanting into the ciliary muscle of the subject. A potentiometer/microcomputer can modulate the ciliary muscle signal detected by the sensor(s) into an electrical signal, and a transmitter sends this electrical signal to a micromotor, which causes compression of the IOL via an annular support ring system, causing a change in the IOL shape. The IOL can be part of an IOL complex including a compressible, accommodating IOL, an external lens membrane, and an annular support ring system. The annular support ring system provides a foundation for the micromotor to compress the IOL.

20 Claims, 5 Drawing Sheets

(56) References Cited

U.S. PATENT DOCUMENTS

| | | | | |
|---|---|---|---|---|
| 7,238,201 | B2 | 7/2007 | Portney et al. | |
| 7,261,736 | B1 * | 8/2007 | Azar | 623/6.22 |
| 7,309,943 | B2 | 12/2007 | Henderson et al. | |
| 7,326,246 | B2 | 2/2008 | Brady et al. | |
| 7,334,892 | B2 | 2/2008 | Goodall et al. | |
| 7,390,088 | B2 | 6/2008 | Goodall et al. | |
| 7,416,562 | B2 | 8/2008 | Gross | |
| 7,486,988 | B2 | 2/2009 | Goodall et al. | |
| 7,591,849 | B2 | 9/2009 | Richardson | |
| 7,795,782 | B2 | 9/2010 | Wischnewskij et al. | |
| 7,857,850 | B2 * | 12/2010 | Mentak | A61F 2/1627 623/6.13 |
| 7,941,201 | B2 | 5/2011 | Chiou et al. | |
| 7,964,833 | B2 | 6/2011 | Holladay | |
| 8,425,599 | B2 | 4/2013 | Shadduck | |
| 8,574,295 | B2 | 11/2013 | Roholt | |
| 8,778,002 | B2 | 7/2014 | Blum | |
| 8,900,298 | B2 | 12/2014 | Anvar et al. | |
| 8,919,953 | B1 | 12/2014 | Ho | |
| 8,968,396 | B2 | 3/2015 | Matthews et al. | |
| 9,036,264 | B2 | 5/2015 | Gupta et al. | |
| 9,052,528 | B2 | 6/2015 | Pugh | |
| 9,084,561 | B2 | 7/2015 | Etzkorn | |
| 9,084,673 | B2 | 7/2015 | Dell | |
| 9,111,473 | B1 | 8/2015 | Ho | |
| 9,113,829 | B2 | 8/2015 | Etzkorn | |
| 9,125,736 | B2 | 9/2015 | Kahook et al. | |
| 9,155,614 | B2 | 10/2015 | Blum et al. | |
| 9,220,590 | B2 | 12/2015 | Beer | |
| 9,277,987 | B2 | 3/2016 | Smiley et al. | |
| 9,364,318 | B2 | 6/2016 | Beer | |
| 9,456,895 | B2 | 10/2016 | Shadduck | |
| 2006/0122530 | A1 | 6/2006 | Goodall et al. | |
| 2006/0122531 | A1 * | 6/2006 | Goodall et al. | 600/546 |
| 2006/0136055 | A1 | 6/2006 | Michel | |
| 2007/0005136 | A1 | 1/2007 | Richardson | |
| 2007/0142909 | A1 | 6/2007 | Peyman | |
| 2008/0177170 | A1 | 7/2008 | Roberts et al. | |
| 2010/0331974 | A1 | 12/2010 | Schaper, Jr. | |
| 2010/0331977 | A1 | 12/2010 | Schaper, Jr. | |
| 2011/0040378 | A1 | 2/2011 | Werblin | |
| 2011/0177393 | A1 | 7/2011 | Park et al. | |
| 2012/0046744 | A1 | 2/2012 | Woods et al. | |
| 2013/0184815 | A1 | 7/2013 | Roholt | |
| 2013/0261744 | A1 | 10/2013 | Gupta et al. | |
| 2014/0227437 | A1 | 8/2014 | DeBoer et al. | |
| 2015/0173893 | A1 | 6/2015 | Portney | |

OTHER PUBLICATIONS

PCT/US2013/021663 International Preliminary Report on Patentability dated Jul. 22, 2014 (6 pages).

PCT/US2013/021663 International Publication No. WO 2013/109579, with ISR, published Jul. 25, 2013 (28 pages).

EP Application 13738060.6 European Patent Office Communication, with extended European Search Report, dated Jun. 8, 2015 (7 pages).

PCT/F12009/050622 International Publication No. WO 2010/004094, with ISR, published Jan. 14, 2010 (28 pages).

DeLuca, Carlos J., Surface Electromyography: Detection and Recording. Delsys, Inc, 2002.

Mettingvanrijn, A.C, et al., Low-cost Active Electrode Improves the Resolution in Biopotential Recordings, Academic Medical Center, Medical Physics Department, Meibergdreef 15 1105 AZ Amsterdam, The Netherlands, Oct.-Nov. 1996.

Marques, E.F., et al. Clinical Performance of a New Aspheric Dual-Optic Accommodating Intraocular Lens, Dove Press Journal, Clin Ophthalmology, Nov. 19, 2014.

Bausch + Lomb, Crystalens Advanced Optics (AO) Accommodating IOL, WWW.bausch.com.

Karavitaki, AE, at al. Long-term Visual Outcomes after Crystalens HD introcular lens implantation, Clinical Opthomology, May 22, 2014.

Larkin, Howard, Dual-Optic IOL, Eurotimes, vol. 16; Issue 5, 2011.

U-M Kellogg Eye Center, Kellogg Resident Creates New Intraocular Power Source, www.kellogg.umich.edu, 2014.

EW Supplement: Crystalens AO: Outstanding Vision Quality Across a More Natural Range; ASCRS—EyeWorld, Mar. 2012.

EP 13 73 8060.6, Search Opinion & Supplementary EP Search Report, May 28, 2015.

PCT/US2013/021663, International Preliminary Report on Patentability, Jul. 22, 2014.

PCT/US2013/021663, International Search Report, Apr. 25, 2013.

PCT/US2016/052400, International Search Report & Written Opinion, Dec. 29, 2016.

WO 2010/004094 A1, Published Jan. 14, 2010, with ISR (28 pages).

* cited by examiner

ACCOMMODATING INTRA-OCULAR LENS SYSTEM

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

FIELD OF THE INVENTION

The present invention relates generally to the correction and/or cure of presbyopia, and more particularly to the reliable transduction of an accommodative impulse of the ciliary muscle to an accommodating intra-ocular lens (IOL).

BACKGROUND OF THE INVENTION

The human eye possesses natural accommodation capability, which involves relaxation and constriction of the circular ciliary muscle of the eye, and zonules controlled by the ciliary muscle, by the brain to provide the eye with near and distant vision. This ciliary muscle action is automatic, and varies the shape of the natural crystalline lens to an appropriate optical configuration for focusing light rays entering the eye on the retina. Ciliary muscle relaxation, which is the normal state of the muscle, shapes the human crystalline lens for distant vision. Ciliary muscle contraction deforms the lens for near vision, and the extent of contraction changes the focal length of the lens to the desired endpoint. This change in effective focal length in order to focus on nearby objects is known as accommodation.

Normally the human eye loses its ability to accommodate as individuals reach the age of 40. This condition, known as presbyopia, is typically due to a progressive loss in the elasticity of the lens of the eye, such that the ciliary muscle can no longer exert the necessary deformation of the lens' shape. In addition, the human eye is susceptible to disorders and diseases which attack the crystalline lens, such as cataracts.

Cataracts causing partial or complete blindness are typically treated by removing the crystalline lens and replacing it with an intra-ocular lens (IOL). While conventional IOL's have had great success at restoring vision, they have limited ability for accommodation. The conventional solution to the problem of presbyopia is a prescription for reading glasses or, for individuals who already require glasses to correct other refractive errors such as myopia or astigmatism, a prescription of bifocal or multifocal glasses. This is necessary for the subject's eye to have clear vision of objects at different distances.

Alternative attempts in the art to overcome presbyopia focus on providing implantable IOL's with accommodation ability. Accommodative IOL's have been introduced, for example, which change the shape of the IOL by physically deforming the lens to become more convex for focusing on nearby objects, similar to the way the body's natural crystalline lens focuses. Other accommodative IOL's work by moving the IOL along its optical axis within the orbit of the eye. However, synthetic IOLs implanted in subjects for the treatment of cataracts typically do not have the ability to change shape as do natural lenses. Thus, subjects with synthetic accommodating IOL's still have presbyopia and cannot adequately focus on proximate visual targets due to the reduced flexibility of the IOL relative to the tractive capabilities of the ciliary muscle. Therefore, such subjects experience a degradation of their ability to accommodate.

It is believed that the neuromuscular activity of the ciliary muscle correlates with a person's effort to adjust the focus of the eye. Previously, enhancement of the physical movement of the ciliary muscle has been utilized for IOL accommodation. For example, U.S. Pat. No. 7,060,094 to Shahinpoor et al discloses a circularly distributed assembly of synthetic muscles in the form of mini-bridges for augmenting the contraction force of the ciliary muscle transmitted to the lens. However, it has been difficult to capture the action potential of the ciliary muscle and transfer it with enough force to cause IOL deformation, even when various multipliers such as micropumps or levers are used.

Other inventions aimed at improving the accommodative abilities of implantable IOLs include the following: U.S. Pat. No. 7,334,892 to Goodall et al discloses an adjustable lens system which detects a neural signal and then generates a control signal to drive actuation of an adjustable IOL.

U.S. Pat. No. 5,800,530 to Rizzo, III discloses an implantable and deformable IOL having microelectronic components implanted thereon, in which a micromotor controlled by a distance measuring apparatus changes tension in a band encircling the periphery of the lens to vary its focal length.

U.S. Pat. No. 5,203,788 to Wiley discloses micromotors powered by EMG or ultrasound to change the lens shape, in which each micromotor is responsive to an externally generated control signal for selectively changing the circumference and/or axial position of the lens. The changes made to the lens are not automatic and are not under the control of the subject.

U.S. Pat. No. 4,373,218 to Schacar discloses an expandable intra-ocular lens filled with liquid crystal material which could be activated by an electrical signal originated from the action potential of the ciliary muscle, sensed by an electrode which is sent to a microprocessor by miniature wiring.

While such prior art devices and methods for the surgical correction of presbyopia may be useful for their intended purposes, those developed to date have generally achieved limited success because they are unable to provide adequate accommodation when compared to a healthy natural crystalline lens, are too complex to be practical to construct, or fail to accurately and reliably focus on demand.

As such, it would be beneficial in the art to provide a system and method that provides an enhanced capacity for accommodation of implanted IOLs. It would also be beneficial to detect a signal, such as an action potential, created by the ciliary muscle and to convert this signal to activate micromotors and/or nanomotors implanted into the eye for creating accommodative forces. It would also be advantageous to mimic the force of contraction created by the ciliary muscle onto a native lens, thereby causing an accommodating shape change in an implanted IOL. It would also be advantageous to provide an IOL system that can detect and capture the action of the ciliary muscle and transfer it with enough force to cause adequate IOL deformation and accommodation.

SUMMARY OF THE INVENTION

The present invention relates to a device which causes a change in the shape of a compressible, accommodating intra-ocular lens (IOL) that has previously been implanted to replace the original crystalline lens of a subject, and which typically includes an internal deformable lens having an external membrane, as is known in the art. The IOL is coupled to a sensor, such as an electromyographic (EMG) receiver (or a series of EMG receivers), which detects a signal created by the ciliary muscle around the eye. The receiver then transmits the signal to a signal processor such as a transducer or microprocessor which generates an electrical signal. A transmitter then sends the resultant electrical signal to a micromotor which creates a force of contraction which acts on the IOL. The force of contraction created by the micromotor can mimic that created by the ciliary muscle onto a native lens, thereby causing a shape change in the IOL.

A first aspect of the invention provides a system for causing a change in the shape of a compressible, accommodating intra-ocular lens (IOL) of a subject, the system comprising: (a) an IOL complex comprising a compressible, accommodating IOL; (b) at least one sensor for detecting a signal from the subject's ciliary muscle; (c) a signal processor for receiving and processing the ciliary muscle signal to generate a corresponding electrical signal; (d) a transmitter for transmitting the electrical signal; and (e) at least one micromotor for receiving the transmitted electrical signal and causing a change in shape of the IOL.

A second aspect of the invention provides a system for causing a change in the shape of a compressible, accommodating intra-ocular lens (IOL), the system comprising: (a) an IOL complex comprising a compressible, accommodating IOL, an external lens membrane, and an annular support ring system for providing a means to cause a change in shape of the IOL; (b) at least one sensor for detecting a signal from the subject's ciliary muscle; (c) a microcomputer for modulating the ciliary muscle signal into an electrical signal; (d) a transmitter for transmitting the electrical signal; and (e) at least one micromotor for receiving the transmitted electrical signal and causing the annular support ring system to compress the IOL.

A third aspect of the invention provides a method for causing a change in shape of a compressible, accommodating intra-ocular lens (IOL) in a subject, the method comprising the steps of: (a) implanting at least one sensor for detecting a signal from a subject's ciliary muscle into an eye of the subject; (b) detecting a ciliary muscle signal with the at least one sensor; (c) transforming the ciliary muscle signal into an electrical signal; and (d) transmitting the electrical signal to at least one micromotor, wherein the micromotor causes a change in shape of an IOL upon receipt of the transmitted electrical signal.

The ciliary muscle signal can be in the form of a neuroelectrical impulse, a muscle action potential, a muscle contractile force, a chemical signal, or a combination of these means. The nature and advantages of the present invention will be more fully appreciated after reviewing the accompanying drawings, detailed description and claims.

BRIEF DESCRIPTION OF THE DRAWINGS

The accompanying drawings illustrate embodiments of the invention and, together with a general description of the invention given above, and the detailed description given below, serve to explain the principles of the invention.

DETAILED DESCRIPTION OF THE INVENTION

As defined herein, the term "ciliary muscle" means a ring of striated smooth muscle encircling the eye that controls accommodation for viewing objects at varying distances. The ciliary muscle also regulates the flow of aqueous humor into Schlemm's canal, and has parasympathetic and sympathetic innervation. The terms "ciliary body" and "ciliary complex" are structures that include the ciliary muscle.

The term "ciliary muscle signal" means an action detected at the subject's ciliary muscle, and more specifically means an action relating to the ciliary muscle in the form of a neuroelectrical pulsation, a muscle action potential, a muscle contractile force or movement, a chemical signal, or a combination of these means. The ciliary muscle signal can be electrical/neuroelectrical or chemical/neurochemical in nature, or it can be initiated by mechanical movement of the ciliary muscle.

Figure 1:
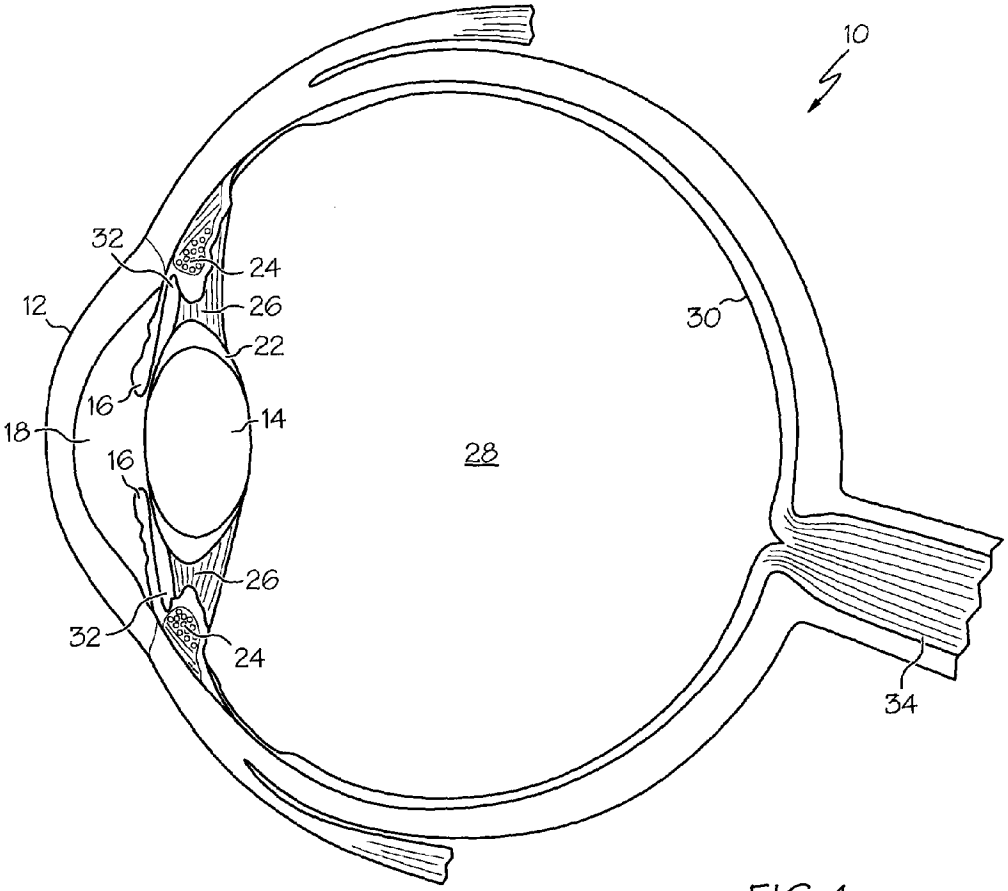
FIG. 1 is a side view illustrating the anatomy of the human eye.

FIG. 1 illustrates a human eye 10, which has an anterior chamber 18 between the cornea 12 and iris 16, a posterior chamber behind the iris containing a bi-convex natural crystalline lens 14, a vitreous chamber 28 behind the lens 14 containing vitreous humor, and a retina 30 at the rear of the vitreous chamber 28. Light is focused by the eye 10 by being refracted through the cornea 12 and then refracted again through the lens 14 and upon the retina 30 for transmission to the brain by the optic nerve 34. The lens 14 is encased in a native lens capsule or capsular bag 22, which is attached about its equator or periphery to the ciliary muscle 24 by zonular fibers 26, called zonules of Zinn. Between the iris 16 and the ciliary muscle 24 is an annular crevice-like space called the ciliary sulcus 32.

While the cornea 12 provides a significant portion of the refractive power of the eye, the capacity for accommodation is primarily contributed by the lens 14, because of its inherent elastic properties. The inner ends of the zonules 26 are attached to the lens capsule 22, and the outer ends are attached to the ciliary muscle 24. The ciliary muscle 24 is part of a sphincter-like ciliary body, which opens when it is relaxed, thereby generating tension on the zonular fibers 26. The ciliary muscle 24 is relaxed in the unaccommodated eye, and the ciliary body therefore assumes its largest inner diameter, which in turn causes a tension on the zonules 26. In this state, the zonules 26 are caused to pull radially outward on the lens capsule 22, flattening and making the lens 14 less convex. Thus, when the ciliary muscle 24 is relaxed, the refractive power of the lens is relatively low and the eye is focused for clear vision of distant objects. The lens capsule 22 is comprised of membrane-like, elastic, optically clear anterior and posterior walls or capsules. When the ciliary muscle 24 contracts the lens capsule moves forward and inward, thereby relaxing the outward pull of the zonules 26 on the equator of the lens capsule 22 and reducing the zonular tension on the lens 14. The lens 14 becomes more rounded, so that the eye is focused for clear vision of nearby objects. Therefore, for near vision, the ciliary muscle contracts and releases tension on the zonular fibers 26, allowing the lens 14 to elastically rebound and thicken, and, in a manner of speaking, "relax" back to its more convex and spherical natural state.

Modern cataract surgery typically involves removing the cloudy contents of the eye's natural lens 14 while leaving the clear outer membrane or capsule 22 (also referred to as a capsular bag) to hold a new, artificial intra-ocular lens (IOL) in place. As illustrated in FIGS. 2-5, a synthetic IOL 15 intended for use in the present invention replaces the natural crystalline lens 14. The IOL can be part of an IOL complex, which can include an internal compressible accommodating IOL 15 which incorporates a flexible, elastic external lens membrane 15a about its periphery, and an annular support ring system 40. The annular support ring system provides a means to cause a change in shape of the IOL. The annular support ring system typically consists of two (2) concentric, adjacent encircling elements: an outer annular support ring 40a and an adjacent inner annular support ring 40b. The inner annular ring 40b encircles, and is attached to, the external lens membrane 15a, which encases the IOL 15. The IOL 15, external lens membrane 15a and the annular support ring system 40a, 40b are all positioned within the native capsular bag 22, which previously encased the (now removed) natural crystalline lens 14 of FIG. 1. The capsular bag 22 and it's supporting zonular ligaments 26 serve as a support structure for the IOL complex and the annular support ring system.

Figure 2:
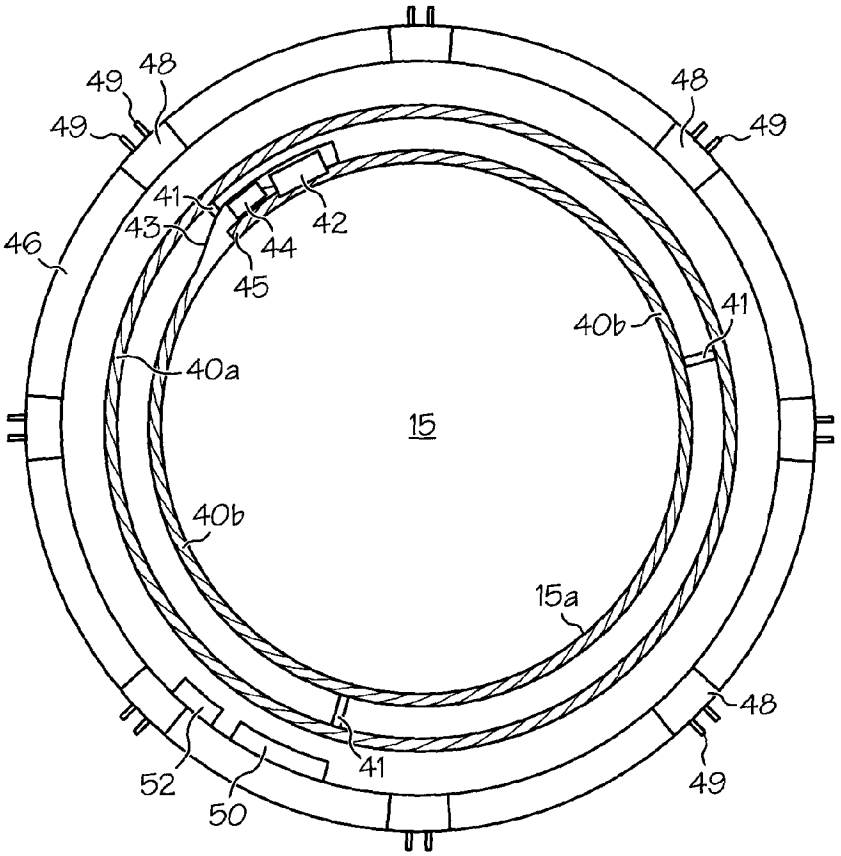
FIG. 2 is a perspective frontal view of one embodiment of the system of the invention.
Figure 3:
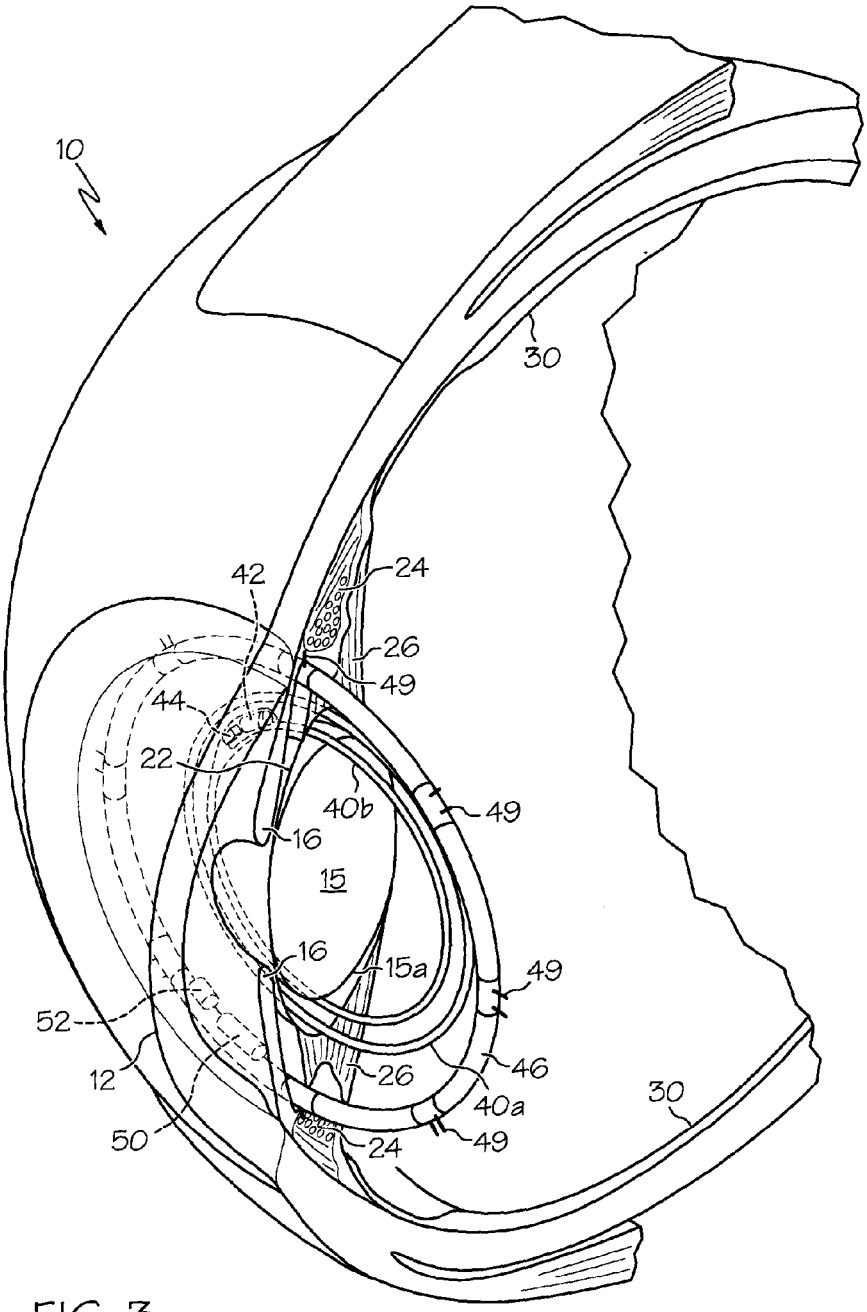
FIG. 3 is a partial cross-sectional view of the human eye showing the embodiment of FIG. 2 after implantation into the eye.
Figure 4:
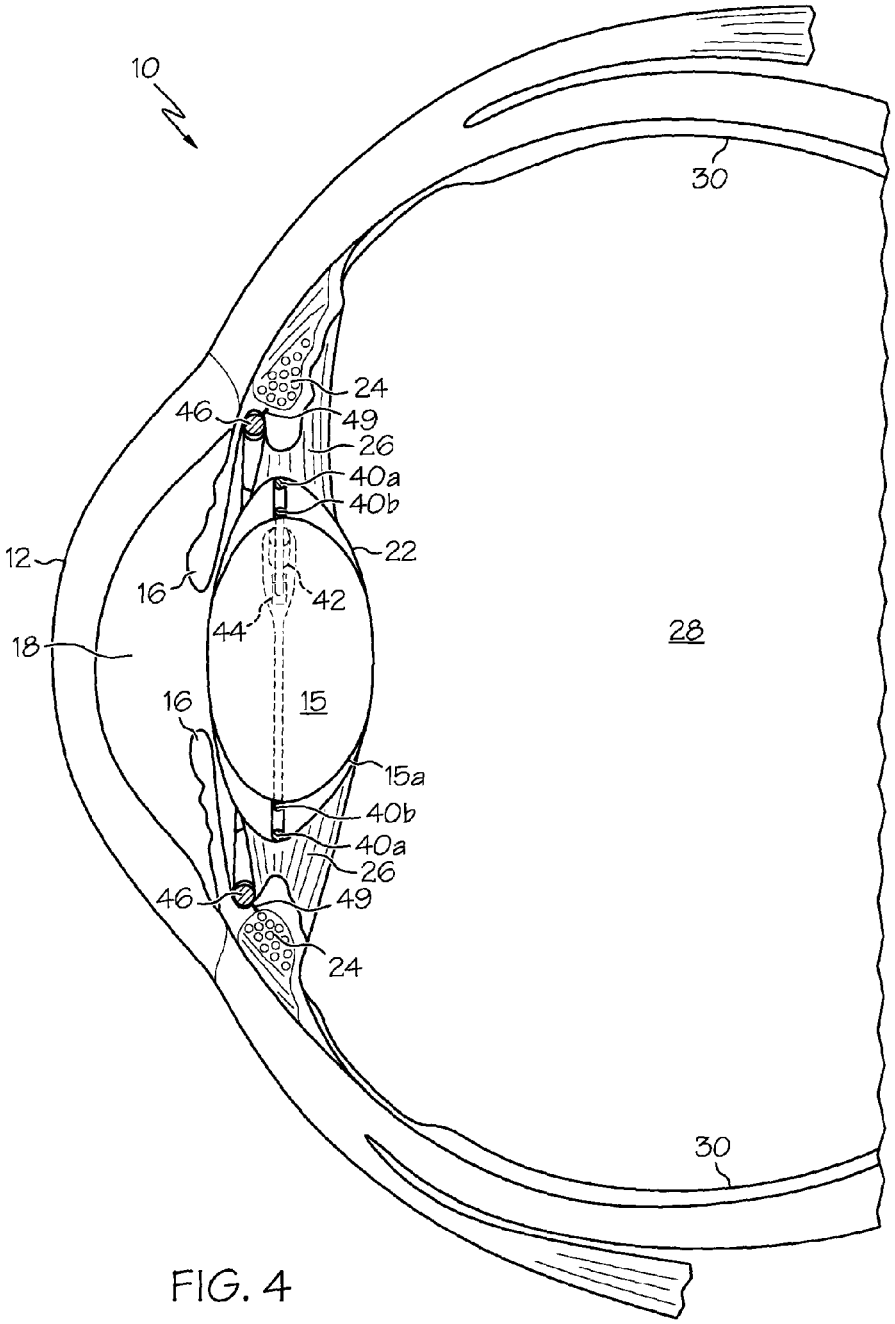
FIG. 4 is a side view illustrating the embodiment of FIG. 2 as positioned within the human eye.
Figure 5:
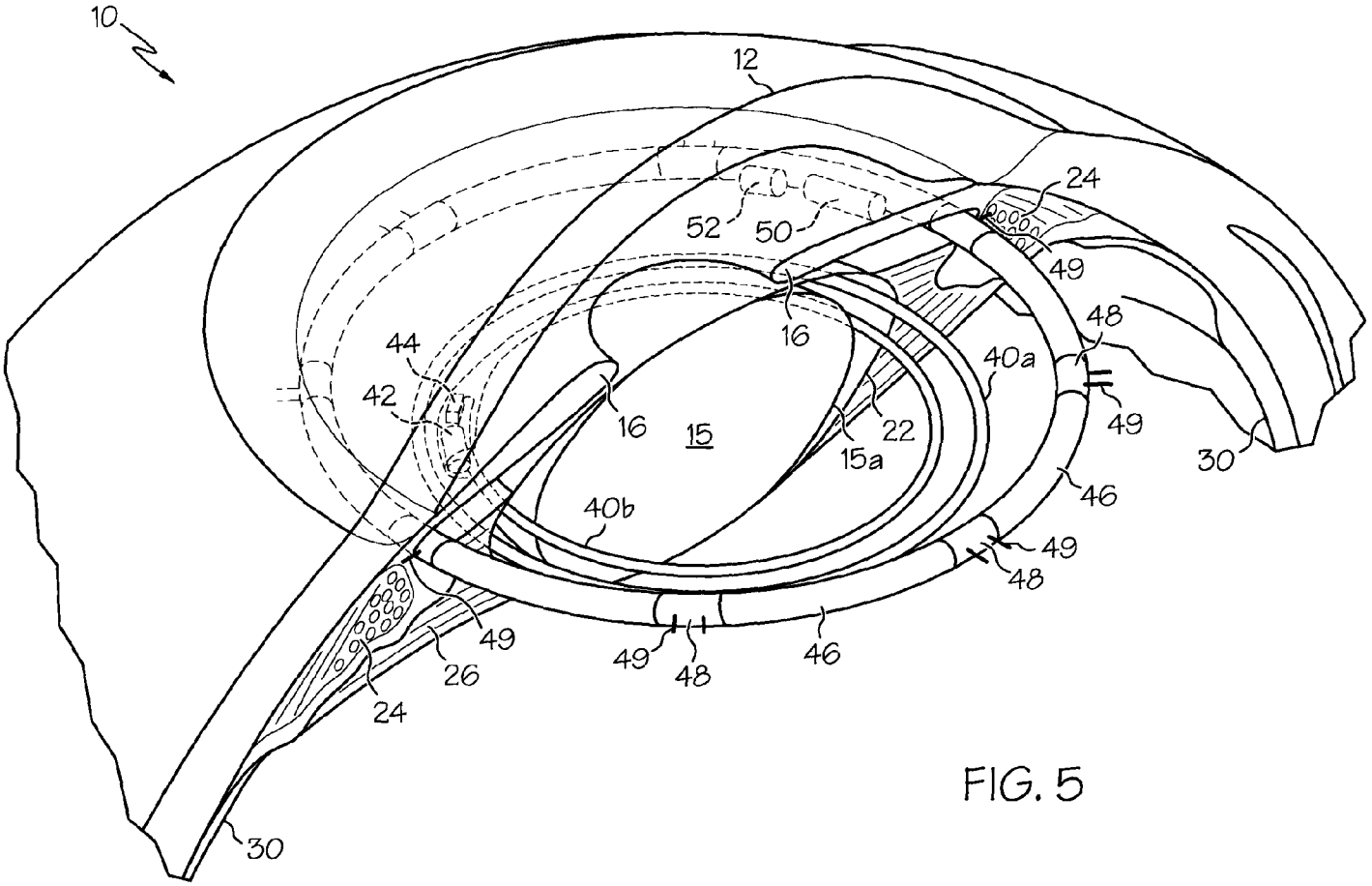
FIG. 5 is a partial cross-sectional view of the human eye showing the embodiment of FIG. 2 after implantation into the eye.

As illustrated in FIG. 2, the inner annular ring 40b encircles the external lens membrane 15a and provides a foundation/housing for a micromotor 42 to cause tightening/shortening of the inner annular support ring 40b, which results in a change in shape of the IOL 15. The micromotor 42 is typically powered by a miniaturized power source such as a rechargeable battery 44. A ciliary sulcus ring 46, which can be implanted in the ciliary sulcus 32 via intra-ocular endosurgery (now commonly and easily performed in a procedure called endocyclophotocoagulation), can communicate with the inner annular support ring 40b via a transmitter 50 (FIG. 2). The ciliary sulcus ring 46 supports at least one and typically a series of ciliary muscle signal sensors 48, illustrated here in the form of electromyographic (EMG) receivers for detecting ciliary muscle contraction. Each EMG receiver 48 can include contacts or miniaturized electrodes in the form of ciliary muscle probes 49, typically in pairs, for entering the ciliary muscle 24 (FIG. 3). However, the invention can employ sensors known in the art that can detect a ciliary muscle signal by electrical/neuroelectrical means, chemical/neurochemical means, mechanical movement of the ciliary muscle, or a combination of these means.

Alternatively, the ciliary muscle signal sensors can be in the form of a first sensor positioned within the ciliary sulcus, typically on the ciliary sulcus ring 46, and a companion sensor positioned on the outer annular support ring 40a. Movement of the first sensor relative to the companion sensor provides the ability to detect ciliary muscle movement in response to the accommodative reflex. Further, a series of ciliary muscle sensors can be supported on both the ciliary sulcus ring 46 and the outer annular support ring 40a, and the degree of movement of these sensors relative to one another can provide very sensitive means for detecting an accommodative signal from the ciliary muscle.

Looking at FIG. 2 it can be appreciated that the inner annular support ring 40b houses the micromotor 42. Activation of the micromotor 42 causes the inner ring 40b to slide upon itself and tighten, thereby shortening the inner ring 40b in both circumference and diameter and exerting a compressive force on the IOL 15 to change the IOL shape. The outer annular support ring 40a can typically be manufactured to be more rigid and adapted to resist compressive, fibrotic contraction forces of the native capsular bag 22. Also, the outer annular ring 40a can include attachments of optical, electrical or magnetic sensors (not shown) with corresponding sensors/receivers located on the ciliary sulcus ring 46. The sensors on the ciliary sulcus ring 46 and the outer annular ring 40a would allow detection of the ciliary muscle action by the relative movement of the two components (40a,46) during accommodation.

As noted above, modern cataract surgery typically involves removing the natural lens while leaving the clear outer capsule 22 to hold the new intraocular lens in place. The capsule 22 that remains has epithelial cells on it which can continue to produce lens fibers. These fibers cannot be laid down in an organized manner and will form little beads or "pearls" on the lens capsule 22, forming a secondary membrane. When these pearls accumulate in the pupil, they cause a blurring of vision similar to that experienced with a cataract. This occurs approximately 30-40% of the time and can appear at any time after cataract surgery, even as much as five or more years later.

Thus, there is a risk that the surrounding capsular bag 22 will scar down, bind, compress, contract and otherwise reduce the effectiveness of a single annular ring. This can be avoided by employing a double ring system as disclosed above, which includes the outer annular support ring 40a and the inner annular support ring 40b of the present invention. With this double annular support ring configuration, the outer annular support ring 40a can protect the inner annular support ring 40b from the contractile forces of a fibrotic capsular bag 22. For example, in FIG. 2 the outer ring 40a is attached to the inner ring 40b via attachment 41 near the location of the micromotor 42 and battery 44 housed on the inner ring 40b. The annular support rings 40a and 40b can also be connected to one another by attachments 41 at intervals along their lengths as shown, if needed for stability, such as every one-third to one-fourth of the way around their circumference. The attachments 41 between the outer ring 40a and the inner ring 40b would likely be via mini-welds or clips.

As shown in FIG. 2, the inner ring 40b includes a free end or distal portion 45 that can fit within the micromotor housing or proximal portion 43, thereby allowing the distal end 45 to slide within itself at the proximal end 43. The housing of the micromotor 42 is typically continuous with the proximal end 43 of the inner ring 40b. This sliding of the inner ring 40b within itself serves to decrease both the diameter and circumference of the inner ring 40b, resulting in a compressive force being exerted upon the IOL. In the embodiment shown in FIG. 2 the inner ring 40b is in a partially compressed position with the distal end 45 located to some extent within the proximal end 43 of the inner ring 40b.

It should be noted, however, that the inner ring 40b cannot have a connection or attachment at its sliding distal end 45 because then the distal end of the inner ring 40b would not be able to slide into its proximal end 43. That is, a sliding inner ring 40b as described here must have a free, unattached segment at its distal end 45, the amount determined by the degree of compression needed as the inner ring 40b is shortened when it slides.

The outer ring 40a not only can provide rigidity to the inner ring 40b in the face of scarring, thereby protecting the inner ring, but as noted above it also can include sensors for detecting relative motion of the ciliary sulcus ring 46. This will allow detection of ciliary muscle action by the relative movement of the two components (40a, 46) during accommodation. In this manner, a first sensor (or series of sensors)

can be positioned on the ciliary sulcus ring 46, and a companion sensor (or series of sensors) can be located on the outer annular support ring 40a, in order to detect relative motion of the ciliary sulcus ring 46 following ciliary muscle movement. Companion sensors can also be placed on the iris or other ocular tissue.

Looking again at FIG. 2, the ciliary muscle sensors 48 can be flat or tubular areas contiguous with the main body of the ciliary sulcus ring 46, and can provide electrical, mechanical or chemical recognition of a ciliary muscle signal via miniaturized electrode probes or contacts 49. A microcomputer and/or micropotentiometer 52 acts as a signal processor and modulates the ciliary muscle signal detected by the sensor 48 and converts it to an electrical signal. This electrical signal created by the microcomputer 52 is then sent to the micromotor 42 via the transmitter 50. Typically a single microcomputer/transmitter system is needed for a ciliary sulcus ring 46; however, it can be appreciated that it may become feasible to attach another set as backup in case of a failure of one of the components. The transmitter 50 can be directly wired to the micromotor 42, or it can work via radio frequency (RF) transmission. The micromotor 42 then creates a tightening of the inner annular ring 40b, and this tightening compresses the compressible IOL 15.

As noted above, the ciliary muscle sensor 48 can be a myoelectrical sensor such as an EMG receiver known in the art for detecting muscle action potentials for taking clinical EMG measurements. With EMG-type sensors, miniaturized electrode probes or contacts 49 are incorporated onto the ciliary sulcus ring 46 and implanted into the ciliary muscle via intra-ocular endosurgery (i.e. via endocyclophotocoagulation). Known EMG electrodes or probes that may be useful as a sensor supported on the ciliary sulcus ring of the invention include those disclosed in U.S. Pat. No. 7,941,201 to Chiou et al., which is incorporated by reference herein in its entirety, disclosing a microprobe array structure suitable for electromyography which detects a neuroelectrical signal through skin.

The ciliary sulcus ring 46 is a generally circular ring which is implanted into the ciliary sulcus 32 of a subject. The ciliary sulcus ring 46 may be made of polymethylmethacrylate, with or without a collamer coating, or a combination of biocompatible metals having conductive plates. If a ciliary sulcus ring includes such conducting plates, the plates can serve as the sensors/EMG contacts 48, and may include fine wire appendages as probes 49 for entering the ciliary muscle. The composition of the probes 49 should be a metal material or an alloy that is both biocompatible and conductive.

Regarding capturing ciliary muscle contraction by mechanical means rather than electrical means, there may be several ways of doing this. For example, a sensor could be fixed to any ocular tissue adjacent the ciliary muscle, near the ciliary sulcus ring, where the relative movement of the companion sensors would be maximized. This could include the outer annular support ring 40a, but can also include the posterior iris base, the external sclera or episclera, or ciliary zonular fibers. Such sensors could detect the relative movement of a companion sensor located on the ciliary sulcus ring.

The diameter of the ciliary sulcus ring 46 may be changed by ciliary muscle contraction, which could be sensed by electrical methods within the ring itself. In one embodiment, the ciliary sulcus ring 46 can be fashioned as a complete circle. Alternatively, in order to facilitate insertion and/or movement, the ciliary sulcus ring can include a space or gap between the ends. Sensors on the ciliary sulcus ring 46 and the outer annular ring 40a would allow detection of the ciliary muscle action by the relative movement of these two components during accommodation.

The micromotor 42 activates the annular support ring system including the inner annular ring 40b around the compressible IOL 15. Since the micromotor 42 is responding to a signal which originated in the ciliary muscle, the action of the micromotor 42 converts the signal created by the ciliary muscle to act on the IOL, causing an accommodation change in the IOL shape. The motor mechanism can be via friction drive, or it can be a sealed, geared motor having a clutch/brake release. Such a micromotor/annular ring combination that may be useful in the present invention is that disclosed in U.S. Pat. No. 5,800,530 to Rizzo, III, incorporated herein by reference in its entirety, which changes tension in a band encircling the periphery of the lens to vary its focal length in response to a distance measuring apparatus. Also, newly developed motors such as piezoelectric motors having a simple, reversible, sliding action, or micromotors such as those disclosed in U.S. Pat. No. 7,309,943 to Henderson, or U.S. Pat. No. 7,795,782 to Wischnewskij et al. may be used, both of which are incorporated herein by reference in their entirety.

As noted above, the micromotor 42 causes the inner annular support ring 40b to compress the IOL 15 and its external membrane 15a,either through piezoelectric action or a geared mechanism. The inner annular ring 40b can accomplish this by sliding upon itself, or into itself, if it is tubular as shown in FIG. 2, to tighten and overlap itself, thereby decreasing in both circumference and diameter. Regarding a tubular embodiment, the ring can be a tapered tube in which the circumference of the sliding end is smaller than the opposite end of the ring, so that the sliding, smaller end can fit inside the larger, stationary end as it slides; alternatively, the sliding end can be larger than the other end of the ring, so that the sliding end can envelop the stationary end as it slides.

The natural accommodative response involves a rapid ciliary muscle contraction, followed by sustained contraction until the accommodative effort is voluntarily released. The mechanisms are not completely understood, but there is presumably an ongoing, continued recruitment of components of the ciliary muscle, such that the ciliary muscle becomes "locked" into place until released. This natural accommodated state is easily maintained, generally without fatigue, until relaxation occurs. When released, the non-accommodated state is attained rapidly, typically in less than ½ sec. In light of this, it is preferred that the micromotor/annular ring combination of the present invention has the ability to release almost instantaneously to the non-accommodated state, and preferably within 0.1 seconds to 0.5 seconds, in order to match the natural speed of accommodation. That is, it is preferable that the inner ring 40b quickly releases the lens 15 so that the lens can return to its original circumference soon after the inner ring 40b undergoes shortening.

Typically the sensor 48, the signal processor 52 and the micromotor 42 are powered by a rechargeable battery 44. Power for the system can be obtained by long-lasting implantable batteries, such as miniature lithium-ion batteries and batteries having lives of up to 50 years, by light-charged batteries through the pupil, or by ciliary complex-activated or ciliary complex-charged batteries. Composite materials for electrochemical storage that may be useful in such a miniature, long-lasting, rechargeable battery of the present invention are disclosed in Published U.S. App. No. 2011/0177393 to Park et al., which is incorporated by reference herein in its entirety. However, any source of electrical power known in the art can be used to run the system.

The method of implanting the device of the invention is technically difficult but can be successfully performed by a skilled ophthalmic surgeon. While the ciliary sulcus ring is relatively easy to implant, since it does not have to be a complete circle, the external annular ring 40a may initially have to include a detachable end that can be directed through a small incision for placement, and then clipped together, making it a complete, rigid circle. The inner ring 40b of course needs to be more flexible so it can be deformed to pass through a 3-5 mm incision. Thus, the inner annular ring 40b, the lens 15 and the flexible membrane 15a can be collapsed and the lens filled by cannula with a low-viscosity refractive polymer after the insertion. After the inner ring and lens complex is inserted, the detachable ends of the outer ring 40a are then clipped together, and the now circular outer ring 40a is then clipped onto the inner ring 40b. Both rings 40a, 40b are typically individually inserted into the anterior chamber, anterior to the iris, and subsequently the entire complex including the rings 40a and 40b and the lens elements 15 and 15a can be easily slipped into the native capsular bag.

In another embodiment of the invention, a thin acrylic circular plate can be implanted first onto the back surface of the native capsular bag 22 prior to implanting the other components of the IOL complex, and would serve as a platform to the other parts of the IOL complex which would be implanted anterior to the acrylic plate. This is done in case a YAG (Yttrium Aluminum Garnet) laser capsulotomy would need to be done due to a secondary cataract. As noted above, continued epithelial proliferation and fibrosis of the lens capsule 22 is a common occurrence with IOLs following cataract surgery. A YAG laser capsulotomy can easily clear the blurred vision produced by a scarred capsular bag 22. The placement of an acrylic circular plate onto the back surface of the native capsular bag 22 would protect the thin, flexible, posterior portion of the external IOL membrane 15a from rupture.

Alternatively, in another embodiment of the invention, the posterior surface of the IOL 15 itself can be made of acrylic. In this embodiment, the posterior surface of the IOL has a fixed curvature, and only the anterior portion of the external IOL membrane 15a is flexible enough to alter the power of the lens 15. These concepts arise because, although some materials are resistant to the YAG pulses, a highly flexible membrane such as that intended for the external IOL membrane 15a may not be. Thus, it is believed that if sufficient compression and shape change of the IOL 15 can be accomplished with only the anterior portion of the external IOL membrane 15a, the posterior portion can be acrylic, which is currently the material commonly used for fixed IOLs.

Taking this concept one step further, another embodiment of the invention can include two separate acrylic plates, one acting as a posterior portion of the lens and the other as the anterior lens. These acrylic plates can replace the IOL 15 (which is typically a fluid- or copolymer-filled bag) and its surrounding flexible membrane 15a. However, the posterior and anterior plates can be connected by a circumferential flexible membrane similar to the IOL membrane 15a, wherein the membrane is acted upon by an intervening movable dual annular support ring system, as described above for the present invention. The acrylic refractive surfaces can be separated by the annular support ring system, and the distance between the plates (lenses) can be changed by the micromotor/ring system, for example by causing the anterior, forward plate to shift forward, thereby adjusting the focus. Examples of inventions utilizing this dual plate technology are disclosed in U.S. Pat. No. 7,118,596 to Zadno-Azizi at al., and U.S. Pat. No. 7,198,640 to Nguyen, both of which are incorporated by reference herein in their entirety.

The present invention utilizes recent advances in microtechnology, including micromotors and/or nanomotors, to convert signals created by the ciliary muscle into contractile forces acting on an implanted IOL. Other advantages of the invention include easy implantability, exceptional optical characteristics, high accommodative range, and excellent natural controllability of refractive effect by accommodative effort and resistance to the natural fibrotic and proliferative forces of the healing capsular bag and intra-capsular epithelium.

While the present invention has been illustrated by the description of embodiments thereof in considerable detail, it is not intended to restrict or limit the scope of the appended claims to such detail. Additional advantages and modifications will be readily apparent to those skilled in the art. Accordingly, departures may be made from such details without departing from the scope or spirit of the invention.

What is claimed is:

1. A system for causing a change in the shape of a compressible, accommodating intra-ocular lens (IOL) of a subject, the system comprising:

a) an IOL complex comprising a compressible, accommodating IOL;

b) at least one sensor for detecting a signal from the subject's ciliary muscle;

c) a signal processor for receiving and processing the ciliary muscle signal to generate a corresponding electrical signal;

d) a transmitter for transmitting the electrical signal; [and]

e) at least one micromotor for receiving the transmitted electrical signal and causing a change in shape of the IOL, the IOL complex further comprising an external lens membrane and an annular support ring system for providing a means to cause a change in shape of the IOL, wherein the annular support ring system comprises two concentric rings including an outer annular ring and an inner annular ring, the outer annular ring being rigid for resisting compressive forces of the native capsular bag, the inner annular ring encircling the external lens membrane and providing a foundation for the at least one micromotor to cause a change in shape of the IOL*; and*

*f) a ciliary sulcus ring adapted for implantation in the ciliary sulcus of the subject and adapted to be positioned around the IOL complex.*

2. The system of claim 1, wherein the at least one micromotor causes a change in shape of the IOL by causing the inner annular ring to shorten in circumference and diameter about the IOL, thereby compressing the IOL.

3. The system of claim 1, [further including a ciliary sulcus ring adapted for implantation into the ciliary sulcus of the subject,] wherein the at least one sensor is an electromyography (EMG) receiver for detecting the muscle action potential of the ciliary muscle, the EMG receiver being positioned on the ciliary sulcus ring and having miniaturized electrodes for implanting into the ciliary muscle.

4. The system of claim [3] *1*, wherein the at least one sensor is a series of EMG receivers positioned about the ciliary sulcus ring, and wherein the signal processor and the transmitter are also positioned about the ciliary sulcus ring.

5. The system of claim 1, wherein the ciliary muscle signal [comprises] *is in a form comprising* a signal selected from the group consisting of a neuro-electrical pulsation, a muscle action potential, a muscle contractile force or movement, and a chemical signal, *or a combination of these signal forms*.

6. The system of claim 1, wherein the signal processor is selected from the group consisting of a micropotentiometer and a microcomputer.

7. [A] *An implantable* system for [causing a change in the shape of a compressible, accommodating intra-ocular lens (IOL),] *correction of presbyopia,* the system, *implantable at an eye of a subject,* comprising:

a) [an IOL complex comprising a compressible, accommodating IOL, an external lens membrane, and an annular support ring system for providing a means to cause a change in shape of the IOL] *a synthetic intra-ocular lens (IOL) sized and configured for implantation at an eye of a subject*;

b) at least one sensor *configured* for detecting a *ciliary muscle* signal from [the subject's] *a* ciliary muscle, *the signal detected at an eye of a subject*;

c) a microcomputer for modulating the ciliary muscle signal into an electrical signal, *the electrical signal used for IOL accommodation*;

[d) a transmitter for transmitting the electrical signal; and e) at least one micromotor for receiving the transmitted electrical signal and causing the annular support ring system to compress the IOL, the system further including]

*d*) a ciliary sulcus ring for implanting into the ciliary sulcus of a subject, the ciliary sulcus ring adapted for supporting at least one [of the at least one] sensor, *the ciliary sulcus ring configured to pass through an incision in the eye of a subject and configured to be proximate to the IOL when implanted at the eye of a subject such that the microcomputer can receive wired or wireless communications from the at least one sensor*.

8. The system of claim 7, wherein the at least one sensor is an electromyography (EMG) receiver *configured* for detecting the muscle action potential of the ciliary muscle, the EMG receiver being positioned on the ciliary sulcus ring and having miniaturized electrodes for implanting into the ciliary muscle.

9. The system of claim 8, wherein the at least one sensor is a series of EMG receivers positioned about the ciliary sulcus ring.

10. The system of claim 7, *wherein*

*the ciliary sulcus ring is part of an annular support ring system adapted to cause a change in focus of the IOL,* wherein the annular support ring system comprises two concentric rings including an outer annular ring and an inner annular ring, the outer annular ring being rigid for resisting compressive forces [of the native capsular bag, the inner annular ring encircling the external lens membrane and providing a foundation for the at least one micromotor to cause a change in shape of the IOL] *developed at a target implant site*.

11. The system of claim 10, [further including a ciliary sulcus ring for implanting into the ciliary sulcus of a subject, and] wherein the at least one sensor includes a first sensor positioned on the ciliary sulcus ring and [a companion sensor] *at least one companion sensor* located on the outer annular support ring.

12. The system of claim 11, wherein the first sensor is a series of sensors and the companion sensor is a series of sensors.

*13. The system of claim 7 wherein the ciliary sulcus ring is a complete circle or is not a complete circle.*

*14. A system for causing a change in the shape of a compressible, accommodating intra-ocular lens (IOL), the system comprising:*

*an (IOL) complex comprising a compressible, accommodating IOL, an external lens membrane, and an annular support ring system for providing a means to cause a change in shape of the IOL;*

*at least one sensor positioned on a ciliary sulcus ring, the sensor for detecting a ciliary muscle signal from a subject's ciliary muscle at an eye of the subject;*

*a microcomputer for modulating the ciliary muscle signal into an electrical signal;*

*a transmitter for transmitting the electrical signal; and*

*at least one micromotor for receiving the transmitted electrical signal and causing the annular support ring system to compress the IOL, wherein the annular support ring system comprises two concentric rings including an outer annular ring and an inner annular ring, the outer annular ring being rigid for resisting compressive forces of an implant subject's native capsular bag, the inner annular ring encircling an implant subject's external lens membrane when implanted and providing a foundation for the at least one micromotor to cause a change in shape of the IOL.*

*15. A system for transduction of an accommodating signal of a ciliary muscle to an accommodating intraocular lens, the system comprising:*

*one or more ciliary muscle accommodating signal sensors,*

*one or more of the sensors configured to detect a ciliary muscle accommodating signal, the accommodating signal reflected in the form of a neuro-electrical pulsation, a muscle action potential, a chemical signal or a combination thereof,*

*the one or more ciliary muscle accommodating signal sensors positioned on a ring, the ring configured to surround an intraocular lens, and configured to permit placement of the ring through an incision in the eye of a patient.*

*16. The system of claim 15 wherein the signal sensors are sized to be implanted in the eye of a patient and wherein the ring is circular.*

*17. The system of claim 15 wherein the signal sensors are sized to be implanted in the eye of a patient and wherein the ring is a complete circle or is not a complete circle.*

*18. The system of claim 15 wherein the accommodating signal is reflected in the form of at least one of: a neuro-electrical pulsation or a muscle action potential or a chemical signal.*

*19. The system of claim 15 wherein one or more of the signal sensors are positioned about an implantable synthetic intra ocular lens (IOL).*

*20. The system of claim 15 further comprising:*

*a plurality of muscle probes, the muscle probes positioned and sized for contact with a ciliary muscle of a patient when implanted in the eye of a patient.*

* * * * *